United States Patent [19]

Ziegler

[11] Patent Number: 4,609,454

[45] Date of Patent: Sep. 2, 1986

[54] OXYGEN MEASURING SENSOR

[75] Inventor: Bodo Ziegler, Stuttgart, Fed. Rep. of Germany

[73] Assignee: Robert Bosch GmbH, Stuttgart, Fed. Rep. of Germany

[21] Appl. No.: 731,466

[22] Filed: May 7, 1985

[30] Foreign Application Priority Data

May 16, 1984 [DE] Fed. Rep. of Germany ....... 3418142

[51] Int. Cl.[4] .......................................... G01N 27/46
[52] U.S. Cl. .................... 204/427; 204/408; 204/428
[58] Field of Search ................. 204/1 S, 421–429, 204/408; 219/270, 553

[56] References Cited

U.S. PATENT DOCUMENTS

| 550,686 | 12/1895 | McLaughlin | 219/270 |
| 2,030,937 | 2/1936 | Reichmann | 219/270 |
| 4,155,827 | 5/1979 | Maurer et al. | 204/428 |
| 4,339,320 | 7/1982 | Friese et al. | 204/428 |
| 4,415,878 | 11/1983 | Novak | 338/34 |
| 4,526,672 | 7/1985 | Reed | 204/428 |
| 4,847,113 | 8/1982 | Fischer et al. | 204/428 |

FOREIGN PATENT DOCUMENTS

| 0056837 | 8/1982 | European Pat. Off. | 204/428 |
| 3035608 | 5/1982 | Fed. Rep. of Germany . | |
| 3237628 | 10/1983 | Fed. Rep. of Germany . | |
| 2017926 | 10/1979 | United Kingdom . | |

Primary Examiner—T. Tung
Attorney, Agent, or Firm—Frishauf, Holtz, Goodman & Woodward

[57] ABSTRACT

A rodlike ceramic member of a heater projects towards and into the active tip of the solid electrolyte tube of an oxygen sensor, extending out from the bottom end of the principal insulating member of the sensor which is made of the same ceramic material. Conducting paths of the heater are brought up to a shoulder where the wider insulating part joins with the carrier of the heater, for connection with conductors leading to the end of the main insulator which is remote from the measuring gas and, furthermore, on this shoulder, connections are also made between conducting paths of the solid electrolyte sensor probe and conductors leading to the end of the main insulator remote from the measuring gas. At that end of the main insulator, sleeve connections are made to connection wires for external connections.

5 Claims, 3 Drawing Figures

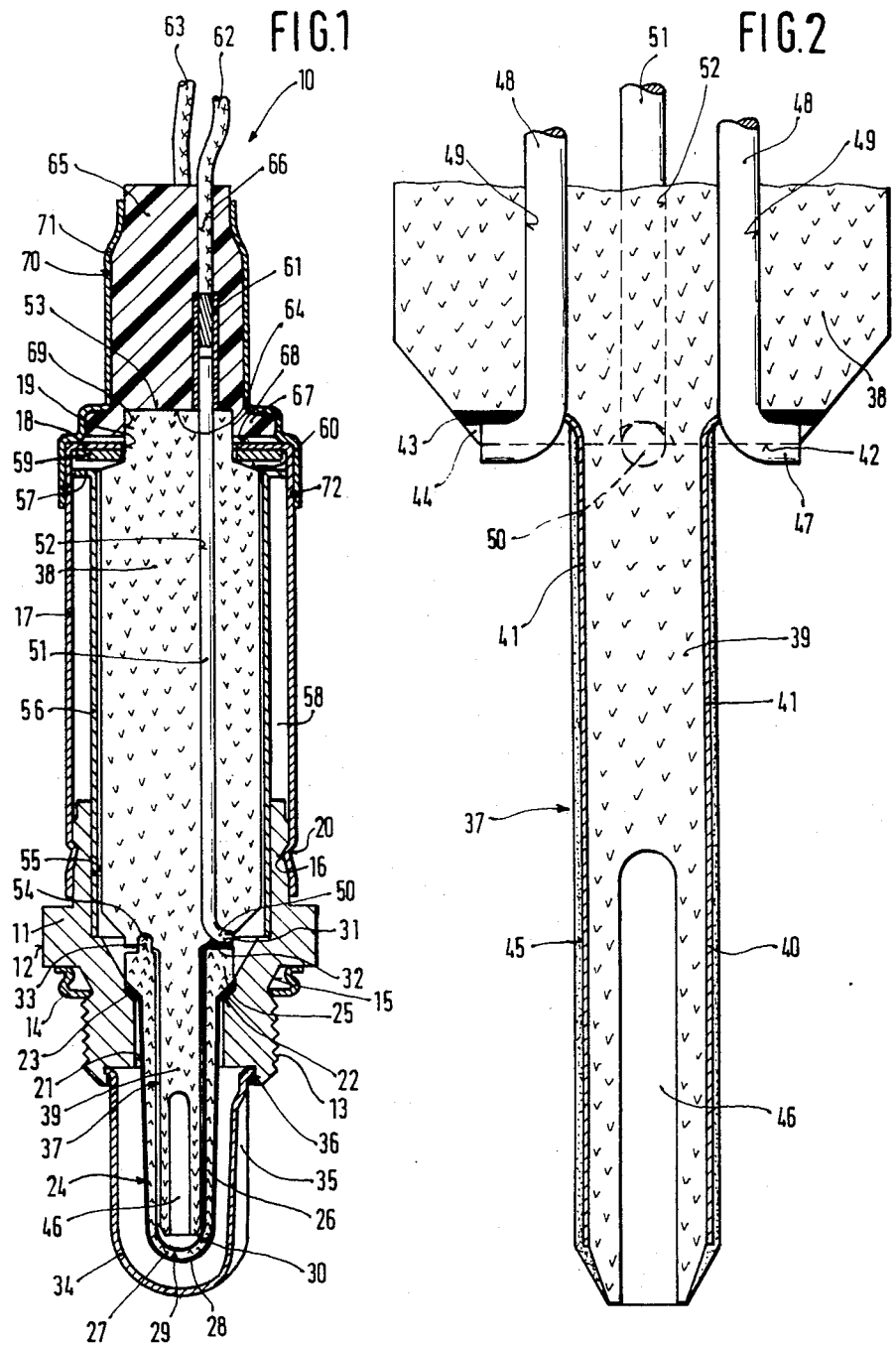

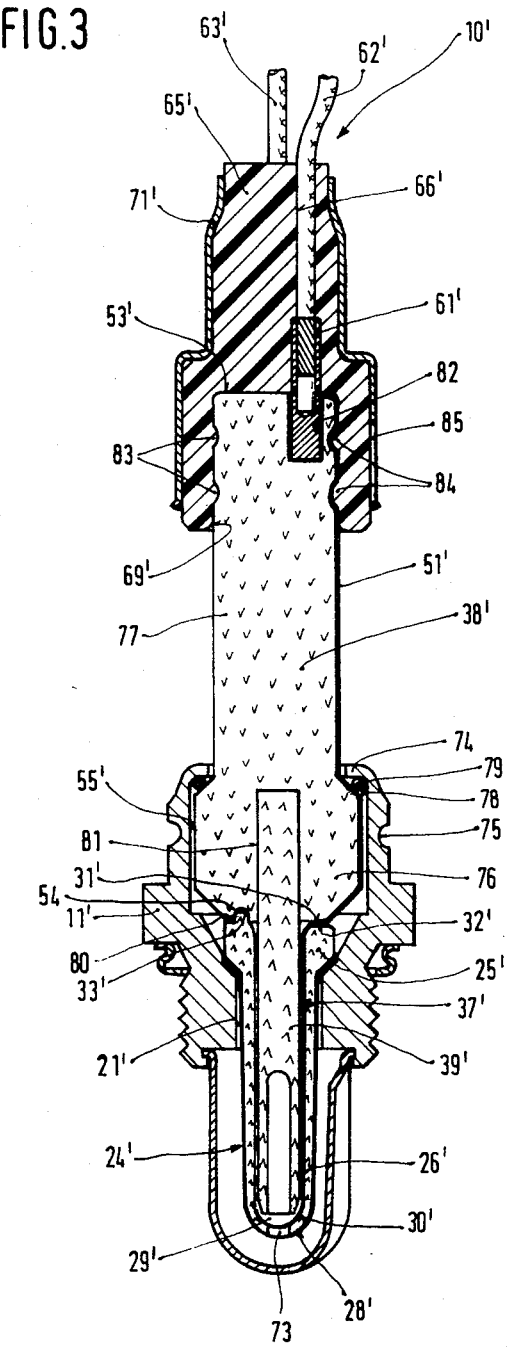

OXYGEN MEASURING SENSOR

The invention concerns an oxygen measuring sensor having a metal casing adapted for mounting in a pipe in which the gas to be measured flows providing a stepped logitudinal bore which holds and seals fast, at least part of the length of a tubular ceramic structure. The latter includes a tubular piece of a material conducting oxygen ions, usually closed at its projecting end, exposed to gas flow, preferably carries an electrode covered with a porous protective layer, has preferably a porous counter-electrode layer on its inner surface, contains an electric heating body in its inner chamber and carries a contact layer for at least one of the two electrodes on its end section remote from the gas to be measured.

An oxygen measuring sensor is already known from the German utility model No. 81 01 584 in which an electrical heating body is built into the inner chamber of its sensor element. In this sensor, the internal construction is relatively complicated and, accordingly, expensive because of the presence of the heating body and its electrical connections.

SUMMARY OF THE INVENTION

It is an object of the present invention to simplify the internal construction of an oxygen sensor of the above described kind, and at the same time to make the sensor less difficult to assemble. It is a further object of the invention to make the sensor more sturdy and shake-proof than previous sensors of the above-described kind.

Briefly, the electrical insulating part carries the electrical heating body as a prolongation at its end section extending towards the measurement gas. Furthermore, the same electrical insulating part also guides at least one electrical connection for the heating body and has an indexing feature by which electrical contact regions on the electrical insulating part are held against corresponding contact regions on the solid electrolyte tube.

The oxygen sensor of the invention has the advantage that its internal construction is simplified and consequently it can be assembled more easily. It also has the desired sturdiness and resistance to vibratory forces.

It is particularly advantageous for the electrical insulating part and the heating body to be combined in a single integral component, because the manufacture of such sensors is made still cheaper thereby and the shake-proof quality of the product is also increased. To the extent that electrical connections on the electrical insulating part of the sensor are constituted as electrically insulated conducting strips, the above-mentioned advantages become more significant.

BRIEF DESCRIPTION OF THE DRAWINGS

The invention is further described by way of illustrative example with reference to the annexed drawings, in which:

FIG. 1 is a longidudinal section through a first embodiment of the oxygen measuring sensor of the invention, on a magnified scale;

FIG. 2 is a longitudinal section through the end section towards the measuring gas of the electrically insulating part of the electrical heating body of the sensor as shown in FIG. 1 drawn on a still further magnified scale, and FIG. 3 is a longitudianl section through a second embodiment of an oxygen measuring sensor, again on a magnified scale.

DESCRIPTION OF THE ILLUSTRATED EMBODIMENTS

The oxygen measuring sensor 10 illustrated in FIGS. 1 and 2, has a metallic casing 11, which is externally provided with a hexagonal portion 12 for engagement by a wrench and with screw threads for screwing into a measurement gas tube, for example, the exhaust pipe of a motor vehicle, not shown in the drawing. An annular seal element 14 serves for sealing the casing 11 in the pipe through which the gas to be measured flows. The seal 14 is positioned in a ring groove 15 located between the hexagonal portion 12 and the threads 13, and thereby kept from getting lost. Another ring groove 16 is machined or otherwise formed into the end section of the casing 11 remote from the measurement gas and serves for fixing the position of a closure shell 17 which prolongs the casing 11. The closure shell 17, which has a cap flange 18 surrounding a central opening 19 at its end remote from the measurement gas, is fixed in place by indentations 20 which are caused to project into the ring groove 16 by stamping or pressing.

The casing 11 has a longitudinal bore 21 providing a shoulder 22 facing away from the measurement end of the sensor 10 can carrying an annular metallic seal element 23. A sensor element 24 lies with its head 25 on the seal element 23 and the shoulder 22 of the casing bore 21.

In the illustrated case, the sensor element 24 is an oxygen measuring probe of an aleady known type known from the above-mentioned German utility model No. 81 01 584, for which there is a corresponding description in English in abandoned U.S. application Ser. No. 326,504, filed Dec. 2, 1981, the contents of which are hereby incorporated by reference. Such an oxygen measuring probe is particularly useful for measuring the oxygen partial pressure in the exhaust gas of internal combustion engines and furnace installations. The probe 24 has a solid electrolyte tube 26 consisting of zircon dioxide that is closed off by means of a floor or tip portion 27 at the end of the tube at the measurement gas end of the sensor. On its external surface exposed to the measurement gas, the solid electrolyte tube 26 is provided with a layer-like gas-permeable measuring electrode 28 and on its surface facing the interior space 29 it is provided with a layer-like counterelectrode 30 which is gas permeable and is exposed to a reference gas (e.g., air). The electrode 30 hence may also be referred to as a reference electrode. In order to increase the service life of the measuring electrode 28, which usually consists of a thin layer of platinum, the measuring electode 28 is, in accordance with well known practice, coated with a gas-permeable protective layer, not shown in the drawing, which, for example, can consist of magnesium spinel.

Instead of consisting entirely of an oxygen ion conducting material, such as zirconium dioxide, the solid electrolyte tube 26 can also be constituted that only the measuring region consists of oxygen ion conducting material, while the remaining length consists of other material, preferably another ceramic material, for example aluminum oxide.

Whereas the measuring electrode 28 is held in contact through the annular metallic seal element 23, with the casing 11 which is electrically grounded (e.g., to the metallic structure of a motor vehicle), the reference electrode 30 preferably extends from the interior surface of the tip 27 all the way to the end surface 31 of the tube 26 remote from the measurement gas and there provides a contact region 32 on a portion of the end surface 31. Between the contact region 32 of the reference electrode 30 and the end surface 31 of the tube 26, an electrical insulating layer is preferably provided which can, for example, consist of aluminum oxide, this layer not being shown in the drawing. A convex indexing projection 33 is provided in the configuration of the solid electrolyte tube 26 for reasons later described.

The section of the sensor probe 24 projecting out of the longitudinal bore 21 of the casing 11, towards the measurement gas end of the sensor, is surrounded by, and spaced from a protective tube 34 which has apertures 35 for the inlet and outlet of a measurement gas and is fixed onto the measurement gas end of the casing 11 by upsetting or some other known means of attachment. The protective tube 34 serves to prevent both the high range of temperature fluctuation occurring in the measurement gas and particles contained in the measurement gas from having direct effect on the sensor probe 24 and causing damage thereto.

The interior space 29 of the solid electrolyte tube 26 is almost all filled by a rodlike electrical heating body 37 which extends almost to the closed tip 27 of the solid electrolyte tube 26. At its end remote from the measurement gas, the main structure of the heater, the carrier 39 for the actual heating element 40, is integrally joined with the electrical insulating part 38. The carrier 39 for the heater and the insulating part 38, are preferably molded and fired in one piece of a ceramic, such as aluminum oxide, for example. The heating element 40 is preferably constituted as a conducting path on the ceramic located substantially in that region of the solid electrolyte tube 26 which forms the measuring region of the sensor probe 24. This heating element 40, which, for example, can consist of platinum, is extended over corresponding conducting path connecting strips 41 all the way to a shoulder 42 of the electrical insulating part 38. The shoulder 42 appears where the heating element carrier 39 joins the remainder of basic portion of the electrical insulating part 38.

The sections of the heating element connections 41 located in the region of this shoulder 42, are preferably somewhat thickened and thus constitute contact regions 43. In the illustrated configuration of the electrically insulating part 38, these contact regions 43 are disposed in indexing troughs of the shoulder 42 which run radially towards the heating element carrier 39.

The heating element 40, constituted in conducting path form, and its similar electrical leads 41, are covered, except for the contact regions 43, with an electrically insulating layer 45 that can, for example, consist of aluminum oxide or magnesium spinel. The heating body 37 consisting of the carrier 39, the heating element 40, its connecting leads 41 and the electrically insulating layer 45, to a great extent fills up the interior space 29 of the solid electrolyte tube 26. In order to produce the heating up of the heater body 37 as fast as possible in the particular region of the sensor probe 24 in which the actual measurement process takes place, the heating element carrier 39 end section towards the measurement gas is provided with a blind axial bore 46 so that this end section of the heating element carrier 39 has a reduced volume of material needing to be heated up. This bore 46 can also serve, in manufacture of the electrical insulating part 38, including its heating element carrier 39, for mounting and positioning the body, as for example during printing on of the heating element 40 and its connecting lead 41.

Contact ends 47, bent at right angles, of wire connecting means 48, which pass through longitudinal bores 49 in the electrical insulating part 38, lie against the contact regions 43 of the heating element 40. These contact ends 47 of the wires 48, lie, towards the measuring gas end of the sensor, on the end face surface 31 of the solid electrolyte tube 26, but in regions which are electrically insulated against the contact region 32 of the reference electrode 30 which also ends on the end face 31 of the tube 26.

A bent over contact end 50 of a connecting wire 51 likewise lies against the contact area 32 for the reference electrode 30. The wire 51 likewise runs through a longitudinal bore 52 of the electrical insulating part 38 and, just as in the case of the connections 48 for the heating element 40, protrudes with its end section remote from the measurement gas out of the end surface 53 of the electrical insulating part 38.

An indexing hole 54 is a feature formed into the shoulder 42 of the electrically insulating part 38. An indexing projection 33 of the solid electrolyte tube 26 extending from the end surface 31 thereof, fits into the hole 54, as a result of which the contact ends 47 and 50 of the connections 48 and 51 are held in the correct position. Instead of the indexing projection 33 and the corresponding hole 54, however, it would also be possible to put cavities, not shown, in the end surface 31 of the solid electrolyte tube 26, into which the contact ends 47 and 50 would fit and thereby fix the relative positions. In these and any other similar ways of dealing with these connections, the contact end 47 and 50 must be clamped securely between the shoulder 42 of the electric insulating part 38 and the end surface 31 of the solid electrolyte tube 26.

The electric insulating part 38 is substantially cylindrical, preferably consists of ceramic material (e.g., aluminum oxide) and extends as shown at 39 with its connected or integral heating body 37 into a widening bore 55 of the end portion away from the measuring gas of the longitudinal bore 21 of the casing. In this widening bore 55, there is also inserted the lower end section of a metallic guide sleeve 56 which coaxially surrounds the electric insulating part 38. This guide sleeve 56 can be fixed in the widening bore 55 of the casing 11 by a pressfit, by caulking, soldering or otherwise. It has an outward flange 57 at its end away from the measuring gas, which extends laterally almost to the closure shell 17. The annular space 58 between the guide sleeve 56 and the closure shell 17 operates as a barrier against moisture which might otherwise enter into the oxygen sensor 10 in the region between the lower end of the closure cell 17 and the casing 11, along with the air serving as reference gas.

Between the flange 57 of the guide sleeve 56 and the inward cap flange 18 of the shell 17, there is an annular spring element 59 (cup spring) which bears, on the one hand, on the cap flange 18 of the shell 17 and, on the other hand, with mechanical bias, on a shoulder 60 of the electric insulating part 38 facing away from the measurement end of the oxygen sensor 10. As a result of the mechanical bias of the spring element 59, the electrical insulating part 38 is pressed, along with its contact ends 47 and 50 lying against its shoulder 42, onto the surface 31 of the solid electrolyte tube 26, thereby providing a necessary contact pressure in this region.

A metallic connection sleeve 61 is pushed onto each of the end sections of the connecting wires 48 and 51 protruding out of the electical insulating part 38, and then affixed to wire ends by means of a known process such as crimping, soldering, welding, etc. The connection sleeves 61 stand with their ends in the measurement gas direction on the end face 53 of the electrical insulating part 38. The other ends of the connecting sleeves 61 surround the uninsulated end sections of connection wires 62 and 63 for the reference electrode 30 and for the heating unit 37 of the oxygen measuring sensor 10. These uninsulated ends of the connection wires 62 and 63 are fixed in the connection shell 61 by crimping, welding and/or soldering.

In addition to the connection sleeves 61, to the end surface 64 of an elastic insulating plug 65 stands on the end surface 53 of the electric insulating part 38. Bores 66 passing through the plug 65 tightly surround the connection wires 62 and 63 and their connection sleeves 61. On its end towards the measuring gas, the insulating plug 65 is equipped with a flange portion 67, the end surface 68 of which tightly stands on the external surface of the cap flange 18 of the closure shell 17. The end surface 64 of the insulating plug 65 is preferably disposed in a coaxial cavity of the flange portion 67 into which fits the end section away from the measuring gas of the electrical insulating part 38.

A tubular and preferably metallic cap sleeve 71 is disposed against the peripheral surface 70 of the insulating plug 65. A widened end of the cap sleeve 71 fits tightly over the end section of the closure shell 17 and is affixed thereto by means of a few spot welds 72 or other known fastening means, thereby holding the insulating plug 65 under mechanical bias in the longitudinal direction of the sensor 10.

Instead of providing two wire connections 48 for the electrical connections of the heating element 40 and leading them through the sensor unit, one of these connections can be saved by providing the electrical return circuit of the heating element 40 over a conducting path section not shown in the drawing, which leads from the end surface 31 of the solid electrolyte tube 26 all the way to the seal element 23 and connects to the contact region 43 on the shoulder 42 of the electric insulating part 38 serving as electrical return conductor to the grounded casing 11.

FIG. 3 shows a second embodiment 10' of an oxygen measuring sensor in which the sensor probe 24' differs from the sensor probe 24 of FIG. 1 by the fact that interior space 29' of the solid electrolyte tube 26' is not sealed against the measurement gas, and the access of measurement gas is made possible through an aperture 73 in the solid electrolyte tube 26'. In an oxygen sensor 10' of this sort, the measuring electrode 28' consists, in a known manner, of a material (e.g., platinum) which is catalytically more active than the material (e.g., gold) of the reference electrode 30' from the interior side of the solid electrolyte tube 26'. In other respects the construction of the sensor probe 24' corresponds to that of the sensor probe 24 of FIG. 1.

The sensor probe 24' is built into a metallic casing 11', which differs from the casing 11 of FIG. 1, in that its end section remote from the measurement gas is provided with an upset rim 74 and an annular heat shrunk region 75.

In the widening bore 55' of the casing bore 21', away from the measurement gas end of the sensor, the section of the electrical insulating part 38' towards the measurement gas, constituted as the head 76, which forms annular shoulder 78 coaxial with the shaft 77 of the electrical insulating part 38'.

A ring 79, on which the flange 74 of the casing 11' presses, lies against the shoulder 78.

On the end face 80 towards the measurement gas of the head 76 of the electric insulating part 38', is an axially running blind bore 81, in which the end section of a carrier 39' of the heater is fixed, for example, by being sintered in place. For reasons of sintering technology it may be convenient to provide the described combination of the electric insulating part 38' and the heating element carrier 39', and this construction may also be desirable for influencing heat conductivity. The arrangement and configuration of the heating element and its leads, not shown in FIG. 3 but forming part of the embodiment illustrated, likewise the electrical insulating layer, correspond to what is shown in the embodiment according to FIGS. 1 and 2.

On the end face 80 of the electric insulating part 38' towards the measurement gas, connection sleeves 61' for wires 62' and 63' extend above the end surface 53' away from the measurement gas and preferably down into respective blind bores 82 provided in this end face 53'. Three connection sleeves 61' are respectively soldered into the three blind bores 82, each with a preferably massive section extending into the bore 82 and its other end surrounding and holding one of the connection wires 62', 63'. . . . The conducting path connection means 51' for the reference electrode 30' of the sensor probe 24' and also the conducting paths, not shown in the drawing, of the heating body 37', are covered up on the electric insulating part 38' by means of an electrical insulating layer not shown, so that only the contact regions 32' on the end face 80 of the electric insulating part 38' and the regions of these conducting paths lying in the blind bores 82, remain uncovered. As a result of the arrangement of the upset flange 74 and the known heat shrinking process, which is effective in the heat shrinking regions 75 of the casing 11', the end face 80 of the electric insulating part 38' is pressed hard against the end face 31' of the solid electrolyte tube 26' and thereby the electrical connection between the contact region 32' of the reference electrode 30' of the sensor probe 24' with the conducting path connection means 51' is established.

Ring grooves 33 are formed into the peripheral surface of the end section of the electric insulating part 38' away from the measurement gas, into which grooves corresponding annular ridges coaxially provided in an end cavity 69' of an insulating plug 65', are gripped to form a seal. Feedthrough holes 66' run longitudinally through the elastomeric plug 65 tightly surrounding the connection wires 62' 63' and their connection sleeves 61'. The tubular end section of the cap sleeve 71' at the measuring gas end of the sleeve is preferably provided with longitudinal slots 85 for expansion, open towards the measuring gas end of the sleeve 71'.

It should be mentioned that even with this kind of oxygen measuring sensor 10', there can be used, instead of a conducting path serving as an electrical return connection of the heating body 37', an electrically insulated conducting path portion (not shown in the drawing) which is connected over the head 25' of the solid electrolyte tube 26', with the casing 11' of the sensor 10'. As a consequence of the fact that the carrier 39' of the heating body 37' is first made as a separate part and then is built into the electrical insulating part 37' by sintering in the blind bore 81, it is also possible to provide a carrier for the heating element which has a rectangular or other polygonal cross section instead of the rod-shaped carrier 39' with its round cross section.

Just as in the case of the sensor 10 shown in FIGS. 1 and 2, the electric insulating part 38' is provided with an index hole 34' in the end face 80 on its side towards the measuring gas, into which an index stud or projection 33' grips for correctly fixing the sensor probe 24' in position. The stud or projection 33' can conveniently be molded onto the solid electrolyte tube 26' in an early stage of its manufacture.

Although the invention has been described with respect to two illustrative embodiments, it will be understood that still further variations and modifications are possible within the inventive concept.

I claim:

1. Oxygen-measuring sensor having a metal casing adapted for pass-through fastening of the sensor in the wall of a duct carrying hot gas, the interior of said casing having the configuration of a stepped central bore, an at least partly tubular ceramic structure held fixed and gas-tight therein, said ceramic structure having at least a first part thereof of material capable of conducting oxygen ions, which is covered on its external surface by a porous layer-shaped electrode, has on its interior surface a layer-shaped counter-electrode and surrounds an electrical heating device located in the interior space enclosed by said first part of said ceramic structure, said first structure part having a first end nearer and a second end more remote from hot gas flow when said sensor is fastened in a duct wall and having at said second end layer-shaped contact pads in contact with connection conductors which extend away from said hot gas flow to connections with externally continuing conductors in a path determined by an electrical insulation member forming a second part of said ceramic structure, said sensor further having the improvement comprising:

a ceramic heating element carrier (39,39') constituting part of said heating device made as an axial extension of said electrical insulation member (38, 38') which is of smaller diameter than said electrical insulating member, protrude into said interior space of said first ceramic structure part made of oxygen-ion-conducting material and has a blind bore (46,46') running axially of the sensor, from the end of said carrier (39,39') nearer said gas flow in the direction of said electric insulation member (38,38');

elongate electrical conductor means (48) in a path determined by said electric insulation member (38,38') for connection to a heating element located on said carrier of said heating device;

electrical contact pads on said electric insulation member electrically connected with said elongate electrical conductor means;

a solid electrolyte tube (26, 26') constituting said oxygen-ion-conducting-material first part of said ceramic structure, having a tubular portion surrounding laterally said heating element carrier (39, 39') and a tip portion extending beyond said end of said carrier and being held against said electric insulation member (38,38') in said casing (11, 11') and positioned firmly with respect to said electric insulation by interfitting indexing configurations of said tube and said member.

2. Sensor according to claim 1, in which said ceramic heating element carrier (39), the remainder of said electrical heating device, and said electrical insulation member constitute a single fully cohesive body.

3. Sensor according to claim 2, in which the outer diameter of said electrical heating device is smaller than the outer diameter of said electric insulation member, so that a shoulder (42, 80) is formed where said electrical heating device adjoins said electric insulation member, and in which at least one of said electrical contact pads on said electric insulation member is located on said shoulder.

4. Sensor according to claim 3, in which said elongate electrical conduction means (48) and said connection conductors (51) are constituted of wires respectively guided in passages running lengthwise in said electric insulation member.

5. Sensor according to claim 3, in which said elongate electrical conduction means and said connection conductors are constituted as conducting paths running on the surface of said electric insulation member which paths are covered by an electrically insulating layer except at contact portions of said paths at their respective ends.

* * * * *